(12) United States Patent
Sigurdsson et al.

(10) Patent No.: US 11,533,920 B2
(45) Date of Patent: Dec. 27, 2022

(54) SYSTEM AND A METHOD FOR PROCESSING MEAT PIECES

(71) Applicant: MAREL ICELAND EHF, Gardabaer (IS)

(72) Inventors: Arni Sigurdsson, Mosfellsbae (IS); Agust Örn Einarsson, Reykjavik (IS)

(73) Assignee: MAREL ICELAND EHF, Gardabaer (IS)

( * ) Notice: Subject to any disclaimer, the term of this patent is extended or adjusted under 35 U.S.C. 154(b) by 644 days.

(21) Appl. No.: 16/349,491

(22) PCT Filed: Nov. 14, 2017

(86) PCT No.: PCT/EP2017/079185
§ 371 (c)(1),
(2) Date: May 13, 2019

(87) PCT Pub. No.: WO2018/087390
PCT Pub. Date: May 17, 2018

(65) Prior Publication Data
US 2020/0187513 A1     Jun. 18, 2020

(30) Foreign Application Priority Data
Nov. 14, 2016   (EP) .................................... 16198637

(51) Int. Cl.
*A22C 17/00*     (2006.01)
*G01N 33/12*     (2006.01)
(Continued)

(52) U.S. Cl.
CPC .......... *A22C 17/008* (2013.01); *B07C 5/3416* (2013.01); *G01N 23/18* (2013.01);
(Continued)

(58) Field of Classification Search
CPC .......... B07C 5/3416; B07C 2501/0081; G01N 23/18; G01N 33/12; G01N 2223/1016;
(Continued)

(56) References Cited

U.S. PATENT DOCUMENTS 3,854,586 A * 12/1974 Perkins, III ............. B07C 5/366
                                                            356/229
5,862,919 A *  1/1999 Eason ....................... B07C 5/00
                                                            209/939
(Continued)

FOREIGN PATENT DOCUMENTS

CN          1759694 A      4/2006
CN        101181073 A      5/2008
(Continued)

OTHER PUBLICATIONS

Chinese Office Action from corresponding CN Application No. 201780071510X, dated May 12, 2021.
(Continued)

*Primary Examiner* — Michael McCullough
*Assistant Examiner* — Kalyanavenkateshware Kumar
(74) *Attorney, Agent, or Firm* — Workman Nydegger

(57) ABSTRACT

A system for processing meat pieces includes a radiation inspection apparatus configured to receive a primary stream of meat pieces conveyed by a conveyor and to detect trim products containing undesired objects; a reject device; a control unit configured to operate the reject device using the detected undesired objects as an operation parameter such that the meat pieces containing the undesired objects are separated from the primary stream of trim products; an object remover configured to remove the undesired objects from the meat pieces separated from the primary stream of trim products; and a recirculation apparatus configured to receive the meat pieces after undergoing the object remover
(Continued)

and recirculate it as a secondary stream into the radiation inspection apparatus. The secondary stream is separated from the primary stream, and the radiation inspection is configured to detect whether any remaining undesired objects are in the secondary stream.

10 Claims, 6 Drawing Sheets

(51) Int. Cl.
  *B07C 5/34* (2006.01)
  *G01N 23/18* (2018.01)
(52) U.S. Cl.
  CPC .......... *G01N 33/12* (2013.01); *A22C 17/0006* (2013.01); *A22C 17/0093* (2013.01); *B07C 2501/0081* (2013.01); *G01N 2223/1016* (2013.01); *G01N 2223/618* (2013.01); *G01N 2223/643* (2013.01); *G01N 2223/652* (2013.01)
(58) Field of Classification Search
  CPC ....... G01N 2223/618; G01N 2223/643; G01N 2223/652; A22C 17/008; A22C 17/0006; A22C 17/0073; A22B 5/007
  See application file for complete search history.

(56) References Cited

U.S. PATENT DOCUMENTS

| | | | |
|---|---|---|---|
| 8,820,534 B2 | 9/2014 | Thorsson et al. | |
| 9,066,524 B2 | 6/2015 | Thorsson et al. | |
| 9,439,444 B2 | 9/2016 | Thorsson et al. | |
| 9,591,859 B2 | 3/2017 | Leenan et al. | |
| 9,854,817 B2 | 1/2018 | Elsoee et al. | |
| 2002/0067797 A1 | 6/2002 | Safai et al. | |
| 2003/0036344 A1* | 2/2003 | Sigurdsson | A22C 17/0086 452/150 |
| 2003/0233918 A1 | 12/2003 | Lindee et al. | |
| 2008/0118616 A1 | 5/2008 | Yoo | |
| 2012/0307013 A1* | 12/2012 | Hjalmarsson | A22C 17/0086 348/46 |
| 2013/0199971 A1 | 8/2013 | Thorsson et al. | |
| 2014/0170947 A1* | 6/2014 | Sigurosson | G01N 23/12 452/184 |
| 2014/0326644 A1 | 11/2014 | Thorsson et al. | |
| 2015/0257397 A1 | 9/2015 | Thorsson et al. | |
| 2016/0081360 A1 | 3/2016 | Elsoee et al. | |
| 2016/0165907 A1 | 6/2016 | Leenan et al. | |
| 2016/0232656 A1* | 8/2016 | Taylor | G01G 17/00 |

FOREIGN PATENT DOCUMENTS

| | | |
|---|---|---|
| CN | 102331430 A | 1/2012 |
| CN | 102519962 A | 6/2012 |
| CN | 103264879 A | 8/2013 |
| CN | 105209905 A | 12/2015 |
| CN | 105517443 A | 4/2016 |
| CN | 105707197 A | 6/2016 |
| GB | 2472008 A | 1/2011 |
| JP | 2002168805 A | 6/2002 |
| WO | 2013023778 A1 | 2/2013 |

OTHER PUBLICATIONS

Extended European Search Report from EP Application No. 16198637.7, dated Jun. 7, 2017.

International Search Report and Written Opinion from PCT Application No. PCT/EP2017/079185, dated Mar. 1, 2018.

* cited by examiner

SYSTEM AND A METHOD FOR PROCESSING MEAT PIECES

FIELD OF THE INVENTION

The present invention relates to a system and a method for processing meat pieces.

BACKGROUND OF THE INVENTION

WO2013023778 discloses a system comprising supply means, a radiation inspection facility, a cutting facility, and a reject facility. Meat parts are brought together at an infeed area and fed into the radiation inspection facility by means of a conveyor in a layer of meat parts. Undesired objects are detected by the radiation inspection facility by means of e.g. an X-ray, and a part of the layer of meat parts containing the undesired objects is identified and separated from the layer of meat parts by the cutting facility, e.g. by cutting a strip from the part of the layer containing the undesired object. The identified and separated part of the layer of meat parts containing the undesired objects is rejected by the reject facility from the layer of meat parts. The undesired part is then removed therefrom, typically manually, and the remaining part of the reject is then fed back to the radiation inspection facility where it is checked whether the meat parts containing the undesired objects have been removed or not.

The process of feeding the reject back to the radiation inspection facility is done by temporarily stopping the infeed of the layer of meat parts so as avoid that the reject overlaps with the infeed of the layer of meat parts. Such temporal stopping however reduces the throughput of the system, which can have severe consequences if the amount of reject is high.

SUMMARY OF THE INVENTION

On the above background it is an object of embodiments of the present invention to provide an improved system and a method for processing meat pieces with at least the same yield but higher throughput.

In general, the invention preferably seeks to mitigate, alleviate or eliminate one or more of the above mentioned disadvantages of the prior art singly or in any combination. In particular, it may be seen as an object of embodiments of the present invention to provide a system and a method that solves the above mentioned problems, or other problems.

To better address one or more of these concerns, in a first aspect of the invention a systems is provided for processing meat pieces, comprising:
a radiation inspection apparatus configured to receive a primary stream of meat pieces and to detect undesired objects in the primary stream,
a first reject device,
a control unit configured to operate the first reject device using the detection of the undesired objects as an operation parameter such that meat pieces containing the undesired objects are rejected from the primary stream,
a recirculation apparatus comprising one or more conveyor devices configured to receive and recirculate the rejected meat pieces as a secondary stream of meat pieces into the radiation inspection apparatus, the radiation inspection apparatus further being configured to detect undesired objects in the secondary stream of meat pieces, and
a second reject device, operated by the control unit using the detection of the undesired objects in the secondary stream as an operation parameter, the second reject device being configured to reject the undesired objects from the secondary stream of meat pieces.

Accordingly, since the pieces containing the undesired objects are rejected from the primary stream, which is typically conveyed by any type of conveyor means such a conveyor comprising an endless belt, and recirculated as a secondary stream, it is not necessary to stop the primary stream during the recirculation of the rejected meat pieces. This increases the throughput of the system. This means that irrespective of the amount of rejected meat pieces that need to be recirculated the primary stream will not be influenced, and it may e.g. be continuously running at all time. Also, the undesired objects may be automatically rejected from the secondary stream which makes the system fully automatized. The automatic rejection may be handled by an end-to-end conveyor arrangement and by moving temporarily one end of the conveyor arrangement to create a temporal gap into which the pieces are rejected.

The primary and the secondary streams should, according to the present invention be understood as two different streams that are in no way intermingled together where the secondary stream is e.g. sidewise to the primary stream. They may as an example be separated by some distance, e.g. few centimeters, or may be adjacent to each other and arranged close to each other.

The term meat pieces may, according to the present invention, be understood as any type of meat, e.g. skeletal meat, such as meat trim, fresh and/or frozen meat. The meat may be poultry, fish, pork, cattle, and it could be whole muscles, pieces and it may include fat.

The undesired objects may include bone or a bone fragment, pieces of cartilage, or other objects such as a piece of metal, glass, plastic, bone, or other foreign objects, blood stains, abscess, infections, etc.

As an example, it is not uncommon that e.g. 1000 kg of incoming meat pieces that is to be run through the system contains 50 to 100 bones or bone fragments and other undesired objects to which a part of the meat trim is attached to. The rejected meat pieces typically weighs tens of kilos due to the amount of meat that is attached to and surrounds the undesired objects (typically bones). Thus, this recirculation distributes the rejected meat pieces in the secondary stream as a stream in the form of a thin layer and/or as separated meat pieces in such a way that the undesired objects may easily be removed with a minimum amount of meat attached to it, which increases the yield. Even thought the undesired objects are removed with a minimum amount of meat attached to it, the removal of the undesired objects typically implies the removal of a certain percentage of meat from the secondary stream. Accordingly, the system may be configured for removal of undesired objects in pieces of meat from the secondary stream of meat pieces. The amount of meat removed from the secondary stream may e.g. constitute ⅓ or ¼ of meat that was rejected from the primary stream.

In one embodiment, the first reject device comprises a cutting device positioned between the radiation inspection apparatus and the first reject device, where the cutting device is configured to cut parts from the primary stream, where the meat pieces containing the undesired objects are the cut parts. The control unit may therefore be configured to define a part of a meat piece of the primary stream and to cut that part off from the meat piece to thereby define a smaller meat piece which is rejected. In that way, it is possible to cut e.g. only a "strip" out from the primary stream using e.g. a rotating cutting knife, e.g. a sword knife or the like, in a direction that may be essentially transverse to the transport direction of the primary stream. Other cutting tools could e.g. include a high pressure water jet and the like, where the cut could include cutting around the undesired object(s) so as to reduce further the amount of meat pieces that are rejected with the undesired objects. It is noted that when e.g. a rotating cutting knife such as a sword knife or the like is used, the conveyor conveying the primary stream may comprise two end-to-end arranged conveyors with a space there between at the cutting location in order for the knife to pass through. The cutting device is preferably operated by the control unit using the detected undesired objects as an operation parameter.

In one embodiment, the first reject device is configured to initially make a temporal opening, e.g. via an end-to-end arrangement of conveyors. The first reject device may cooperate with the cutting device such that the meat pieces (meat piece strip) containing the undesired objects are cut and simultaneously rejected by the impact from the cutting device on the end-to-end arrangement through the temporal opening. As an example, the width of the meat piece strip that is to be cut is allowed to pass a free end of an upstream conveyor of the end-to-end arrangement of conveyors followed by said cut such that the cut is followed by an immediate reject through the opening. Subsequently, the free ends of the conveyors are moved back to a closing position. As an example, a moving mechanism may be connected to the free and of the upstream conveyor that moves the end temporarily opposite to the conveying direction for creating said temporal opening. Accordingly, by providing such a simultaneous reject, the overall size of the system may be reduced.

According to a further preferable embodiment, said cutting device and/or the conveyor mean may be designed for creating a distance or an added distance between separated cut parts, e.g. by temporarily slowing down one of the conveyors, or by temporarily accelerating the downstream conveyor. Hereby, it is achieved that the meat pieces that have been cut will not stick to each other after the cutting. Thus, the cutting will result in relatively sharp cutting surfaces and a clear separation. Furthermore, by creating a distance or gap, the subsequent process of rejecting a separated part can be facilitated, i.e. since it is easier to reject a separated part, the risk of interfering with the primary stream of meat pieces is reduced considerably. Thus, hereby the processing or handling speed can also be increased.

In one embodiment, the first reject device further comprises a spacer for creating a temporal spacing adjacent to a cutting plane of the cutting device so as to allow the cut parts to be rejected simultaneously with the cutting. Accordingly, such an immediate rejection of the cut parts allows the system to be more compact. Also, the impact from the cutting device may be utilized to ensure that the cut parts are removed from the primary stream, i.e. the possibility that the cut parts will stick together is reduced or eliminated.

In one embodiment, the system further comprises an object remover configured to remove undesired objects from the rejected meat pieces prior to entering the radiation inspection apparatus as the secondary stream. In that way, a kind of a coarse removal of the undesired objects may be performed prior to generating the secondary stream which may reduce up to a certain extent of the reject at the second reject device. The object remover may e.g. be understood as a manual labor that manually removes the undesired objects e.g. simply via visible detection, or the object remover may e.g. comprise a robotic arm using e.g. a vision detection system, or other device(s) well known to a person skilled in the art.

In one embodiment, the recirculation apparatus comprises a distributing apparatus configured to generate the secondary stream as a substantially even stream, or a stream of separated rejected meat pieces. In an embodiment, the distributing apparatus comprises an auger device. Accordingly, it is ensured that the secondary stream is evenly distributed where it may e.g. be ensured that the property, e.g. the thickness/evenness of the stream or the discreteness of the stream, of the second stream is optimal, which may be important to ensure an optimal reject at the second reject device.

In one embodiment, the recirculation apparatus comprises:
a first conveyor device,
a second conveyor device, the first conveyor device being configured to receive the rejected meat pieces and convey it to the second conveyor apparatus where the rejected meat pieces are conveyed upwards and released such that the secondary stream is generated.

The first conveyor device is accordingly configured to receive the rejected meat pieces that may be dropped down from the primary stream. This may as an example be cut strips containing the undesired objects that are subsequent to the cutting, and which may be dropped down to a first conveyor device. The dropping down may e.g. be done via any kind of means capable of separating the cut parts from the primary stream, e.g. where a temporal opening may e.g. be made between two adjacent conveyors such that the cut parts is dropped down. The first conveyor device may then convey the rejected meat pieces to the second conveyor device, which may e.g. comprise a vertical conveyor that conveys the rejected meat pieces upwards to at least the same height level as the primary stream. The remaining part of the meat pieces may subsequently be released side-wise to the primary stream as the secondary stream. The recirculation apparatus may comprise any known means for handling objects, e.g. a robotic system.

The term conveyor device may, according to the present invention, be understood as a conveyor apparatus comprising an endless conveyor belt, or e.g. any type of an auger device. Accordingly, said first conveyor device may comprise a first horizontally arranged auger device placed below the primary stream configured to receive and advance the rejected meat pieces in a back or forth direction, which may either be opposite to the direction of the primary stream or parallel to the primary stream. The latter instance may be where a piece of metal or glass is detected that is to be removed immediately from the process, instead of recirculating it into the system. Similarly, the second conveyor device may comprise a second vertically arranged auger device arranged at one end of the first auger device that receives the rejected meat pieces from the first auger device and advances it upwards above the height level of the primary stream. There the re-circulated rejected meat pieces are received and released as said secondary stream. A third auger device may be provided to produce said secondary stream in a way that e.g. an automatic reject by said second reject device is enabled, e.g. by creating a spacing there between to allow automatic reject by the second reject device.

In one embodiment, the radiation inspection apparatus comprises an X-ray apparatus. The X-ray technique of the radiation inspection apparatus may operate according to e.g. a single energy technique or a dual energy technique, which is well known to a person skilled within the field of radiation technology and in particular X-ray radiation technology. Such technologies are well-described within the prior art.

In one embodiment, the remaining meat pieces in the primary stream and the secondary stream are conveyed to a common receiving area by at least one conveyor. This common receiving area may as an example comprise an auger device, or a pre-grinder or any type of pre-processing area, or simply a take-away area where the meat pieces are accumulated together.

In one embodiment, the second reject device may comprise one or more of the following: a slidable conveyor or conveyor part, a pivotable conveyor or conveyor part, a rejector or a gripper, a picker or the like, which may also be referred to as reject units. Thus, it will be understood that various means may be used for rejecting meat pieces containing undesired objects and that in general it will be understood that a rejected meat piece may be removed, dropped, lifted and moved, picked and moved, gripped, etc. and generally removed from the primary stream which could e.g. be a layer of meat parts. Thus, it will also be understood that e.g. a robot, a gripper, a picker or the like may be used in connection with the reject facility for controllably rejecting a separated part.

The primary stream may in one embodiment be conveyed by a first conveyor and the secondary stream by a second conveyor arranged sidewise to the first conveyor, where the first and the second conveyors comprise a first and a second endless belts, respectively.

In a second aspect of the invention, a method is provided of processing meat pieces, comprising:
receiving a primary stream of meat pieces,
detecting, by a radiation inspection apparatus, meat pieces containing undesired objects,
using the detection of the undesired objects as an operation parameter in rejecting meat pieces containing the undesired objects from the primary stream,
recirculating the rejected meat pieces as a secondary stream of meat pieces into the radiation inspection apparatus,
detecting, by the radiation inspection apparatus, undesired objects in the secondary stream of meat pieces,
using the detection of the undesired objects in the secondary stream of meat pieces as an operation parameter in rejecting the meat pieces containing the undesired objects from the secondary stream.

Accordingly, a method is provided that enhances the throughput greatly since the primary stream does not need to be temporarily stopped during the recirculation of the rejected meat pieces. Moreover, such a recirculation of the rejected meat pieces distributes the undesired objects.

The method may include removing undesired objects in pieces of meat from the secondary stream of meat pieces. Accordingly, an amount of e.g. ⅓ or ¼ of the meat which is rejected from the primary stream of meat may according to the method be rejected from the secondary stream.

In one embodiment, the primary stream of meat pieces is received in an essentially continuous layer having an essentially even thickness. This may be done by various means, as it will be apparent to a skilled person, for example also by means of e.g. a funnel-shaped arrangement, through which the meat parts are pushed, or by meat layer shaping means arranged for shaping incoming meat pieces into such a continuous layer having an essentially even thickness. The meat layer shaping means may also be in the form of an inclining conveyor belt or the like, which serves to even out incoming meat pieces and furthermore serves to compress the meat pieces into a substantially uniform layer. Other means include any type of guide plate arrangement resulting in that the meat pieces are shaped into a layer or stream of meat pieces having an essentially uniform and rectangular sectional shape, which corresponds to the working capability of the radiation inspection apparatus.

A layer shall be understood as comprising a plurality of meat parts, wherein at least two of these meat parts are touching each other in an essentially continuous stream of meat parts, wherein, although, gaps or distances may be present in the stream of meat parts.

In one embodiment, in case undesired objects are in the secondary stream, the method further comprises separating a portion from the secondary stream from the remaining part of the secondary stream.

In one embodiment, the rejected meat pieces containing the undesired objects in the secondary stream contains less meat than the rejected meat pieces containing the undesired objects from the primary stream.

The step of rejecting the undesired objects from the secondary stream is done fully automatically using any known ways of rejecting items, e.g. by use of robotic arms or by creating temporal opening on the conveyor conveying the secondary stream.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
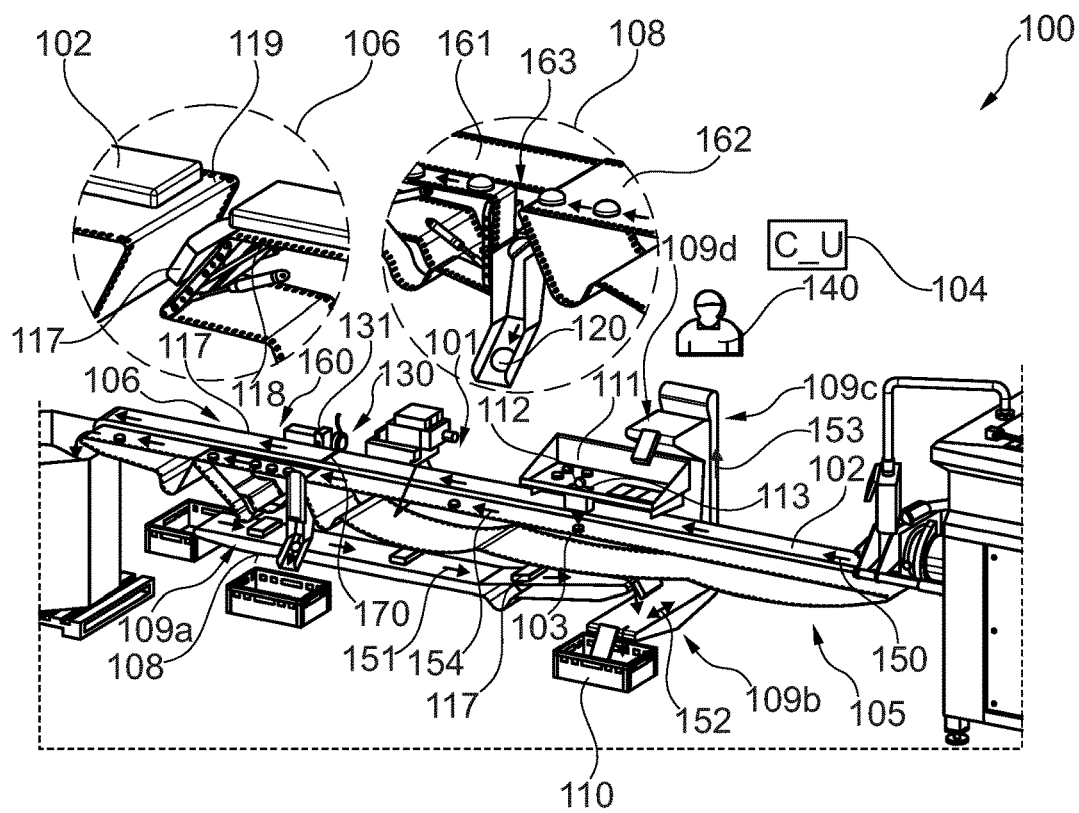
FIGS. 1 and 2 show two embodiments of an embodiment of a system according to the present invention for processing meat pieces.

FIG. 1 shows an embodiment of a system 100 according to the present invention for processing meat pieces. The system comprises a radiation inspection apparatus 101, e.g. an X-ray apparatus, showed here in an absence of a housing (which among other things acts as a shield and absorbs radiation), configured to receive a primary stream 102 of meat pieces conveyed by a conveyor 105 and conveyed in a conveying direction as indicated by arrow 150 and to detect undesired objects 117 in the primary stream. The undesired objects may e.g. include bones or bone fragments, pieces of cartilage or other objects such as pieces of metal, glass, plastic, blood stains, abscess, or infections, etc.

The primary stream 102 is shown as a continuous layer having an essentially even thickness. This may be achieved using a funnel-shaped arrangement, or as shown in FIGS. 1-4 in WO2013023778 disclosing a meat layer shaping means arranged for shaping incoming meat pieces into an essentially continuous layer having an essentially even thickness. The meat layer shaping means may be in the form of an inclined conveyor belt or the like, which serves to even out incoming meat pieces and furthermore serves to compress the meat pieces into a substantially uniform layer. Other means may be used as well, such as any type of a funnel shape arrangement made by any type of guide plate arrangement resulting in that the meat pieces are shaped into a layer or stream of meat pieces having an essentially uniform and rectangular sectional shape, which corresponds to the working capability of the radiation inspection apparatus. Hereby, the capacity of the radiation inspection apparatus will be used in an optimal manner.

The system further comprises a first reject 160 device operated by a control unit 104 using the detection of the undesired objects as an operation parameter such that the meat pieces containing the undesired objects may be rejected from the primary stream 102.

The first reject device 160 shown here comprises a cutting device 130 operated by the control unit 104 using the detection of the undesired objects as an operation parameter. The cutting device 130 is positioned downstream the radiation inspection apparatus and is configured to cut parts from the primary stream 102 containing the undesired objects. As shown here, the cutting device comprises a rotating cutting knife 131, e.g. a sword knife or the like, arranged in a direction that is essentially transverse to the transport direction 150 of the primary stream such that only a part (e.g. a slice) containing the undesired object(s) is cut from the primary stream.

The rotating cutting knife 131 may be position between two adjacent conveyors placed in an end-to-end arrangement, where the gap 170 there between defines the cutting plane of the rotating cutting knife.

Other cutting arrangement may of course be utilized such as, but not limited to, high pressure water jet, laser cutter, robotic operated cutter etc.

The first reject device 160 comprises in this embodiment a reject unit 106 comprising two adjacent conveyors 118, 119 placed in an end-to-end arrangement, where the reject unit 106 is operated, as shown in the zoomed up view, such that the end of the upstream conveyor 118 is temporarily withdrawn causing a temporal opening there between allowing the rejected meat parts 117 to fall down and be removed from the primary stream 102.

The reject unit 106 may operate in accordance with any known way of rejecting objects from a conveyor. It may e.g. comprise a pivotable conveyor or conveyor part, a rejector, or a gripper, a picker, or other devices known for this purpose, i.e. something the removes the rejected meat parts from the primary stream.

The system 100 further comprises a recirculation apparatus 109 configured to recirculate the rejected meat pieces 117 as a secondary stream 103, which as shown here is in a form of separated meat pieces into the radiation inspection apparatus 101.

In this embodiment, the recirculation apparatus 109 comprises a conveyor arrangement comprising a first conveyor device 109a positioned below the reject unit 106 configured to receive the rejected meat piece 107 and convey it in a direction as indicated by the arrow 151 opposite to the direction 150 of the primary stream 102 to a conveyor device 109b, which is arranged essentially perpendicular to the conveying direction 151. Conveyor 109b is capable of operating in back and forth direction as indicated by the arrow 152, where one direction may be a reject into a reject area 110 where a particular meat part may be completely rejected (e.g. metal, glass etc.), whereas the other direction is towards a second conveyor device, which may also be referred to as a vertical conveyor 109c. The vertical conveyor 109c is configured to receive the remaining rejected meat parts, convey them upwards as indicated by the arrow 153 onto a flat conveyor section 109d that may positioned such that the release of the rejected meat parts define the secondary stream.

As shown here, the rejected meat parts may also be released onto a processing table 111, where an operator 140 may manually removes undesired objects that may be visible, before generating the secondary stream by means of releasing the pre-processed meat parts 112, i.e. after removing the undesired objects therefrom, via an opening 113. The released pre-processed meat parts define a secondary stream 103 that is conveyed in a conveying direction as indicated by arrow 154, parallel to the primary stream and through the radiation inspection apparatus 101. The radiation inspection apparatus 101 is further configured to detect whether any remaining undesired objects are in the secondary stream. As shown here, the primary stream does not need to be stopped during this recirculation.

The conveyor carrying the primary and the secondary streams may in one embodiment comprise a dual lane conveyor where one lane conveyor conveys the primary stream and the other lane conveyor conveys the secondary stream. These conveyors are arranged in an end-to-end arrangement of conveyors, respectively, where respective one of the two end-to-end arrangements are operably connected to a moving mechanism for e.g. making the temporary opening for the primary stream as discussed above, and for the secondary stream as will be discussed in more details below.

Those meat parts in the secondary stream containing undesired object 120 may be automatically rejected by a second reject device 108, similar as discussed above, using the detection of the undesired objects in the secondary stream as an operation parameter. This may e.g. be done by making a temporal opening via the above mentioned end-to-end arranged conveyors 161, 162 carrying the secondary stream as shown in the zoomed up view. As shown here, one end of the upstream conveyor 162 is temporarily withdrawn causing a temporal opening 163 there between allowing the undesired object 120 or meat part 120 containing undesired object to be dropped to a reject location.

Removal may generally be carried out in any known way of removing objects from a conveyor, including by manual operation where an operator is notified and removes the meat part manually from the secondary stream.

Figure 2:
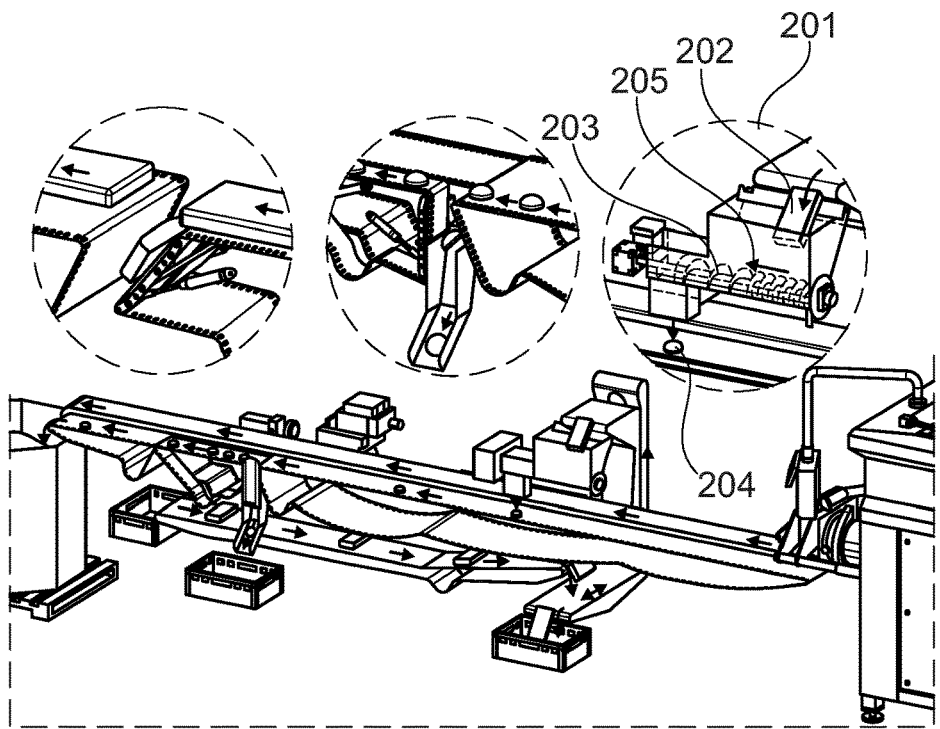

FIG. 2 shows the embodiment in FIG. 1, but where the recirculation apparatus comprises a distributing apparatus 201 configured to generate the secondary stream as a substantially even stream, or as shown here, a stream of separated rejected meat pieces 204. In this embodiment, the distributing apparatus is a conveyor device comprising an auger device 203 that is configured to receive, from the flat conveyor section 109d, the rejected meat pieces 202 and advance the rejected meat pieces in a direction as indicated by arrow 205 where the secondary stream is created.

Figure 3:
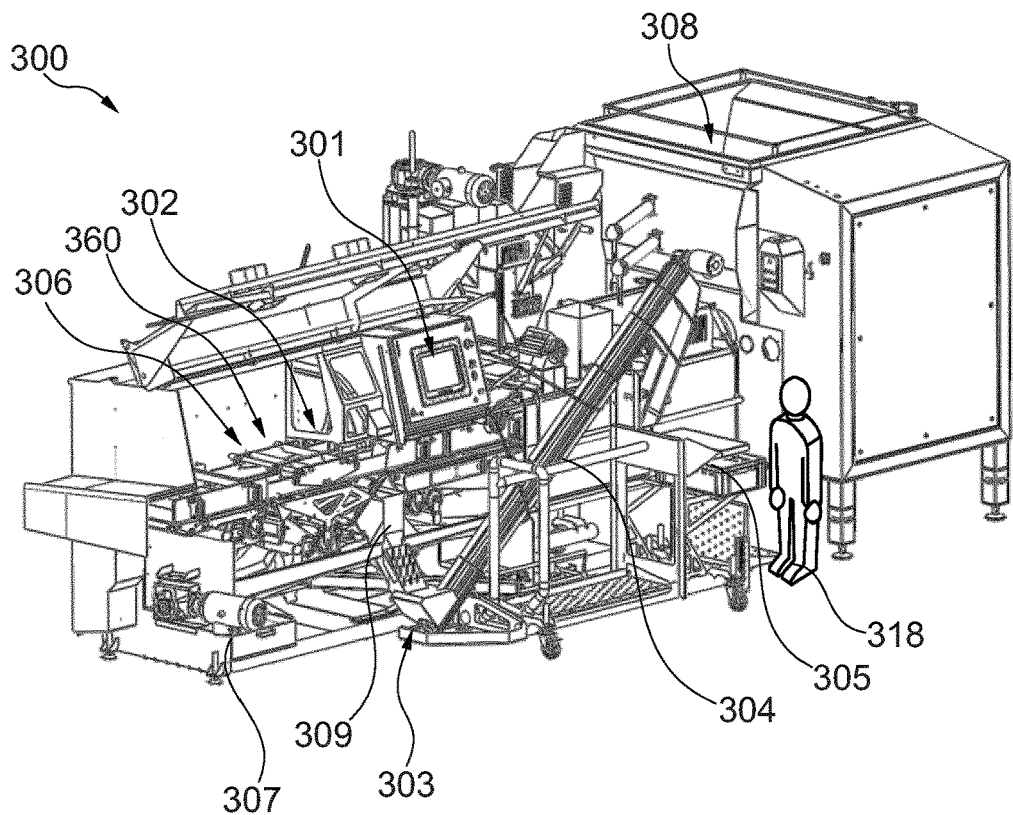
FIGS. 3 and 4 show perspective views of another embodiment of a system according to the present invention for processing meat pieces.
Figure 4:
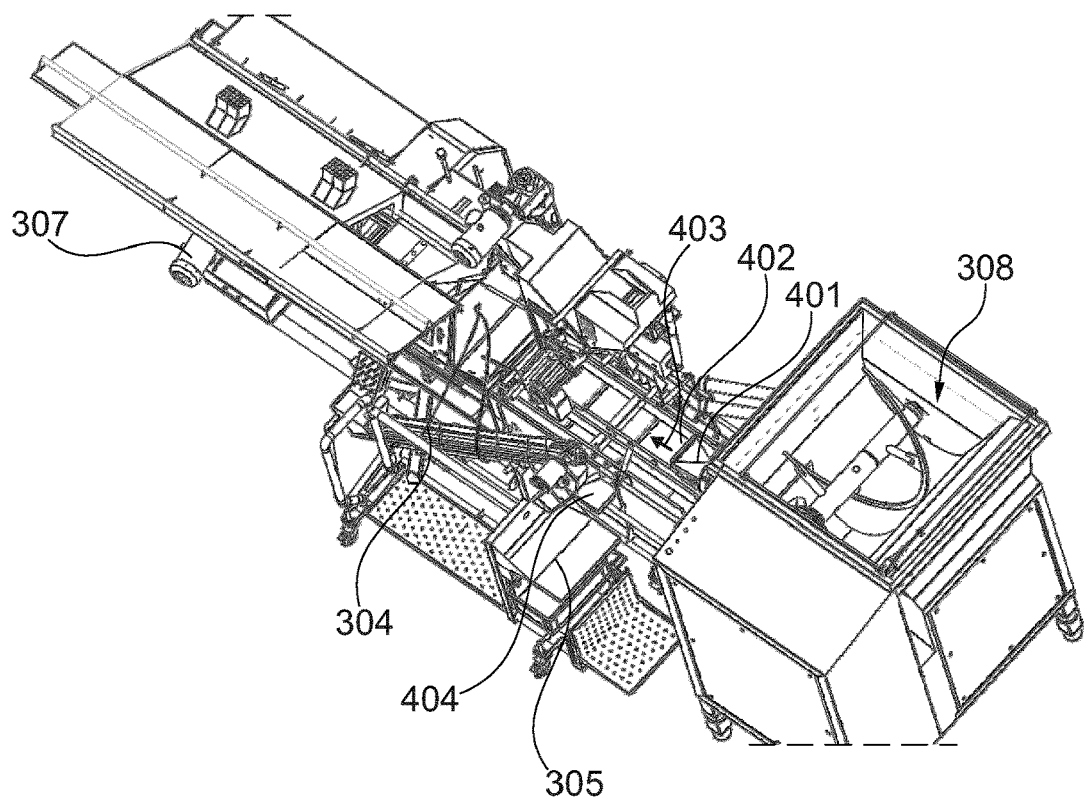

FIGS. 3 and 4 show two different perspective views of another embodiment of a system 300 according to the present invention for processing meat pieces. Shown here is also a meat pump, or a meat grinder, or a pre-grinder 308 which may be considered as an optional feature, where meat pieces such as fresh and/or frozen meat blocks are fed therein, and where the meat e.g. the pre-grinded meat pieces 402 are fed through a funnel/nozzle 401 preferably as an even stream into the system 300 as a primary stream. As will be discussed in more details in relation to FIGS. 5 to 11, the primary stream 402 is conveyed by a first (primary) conveyor device that conveys it in a conveying direction as indicated by arrow 403 through a radiation inspection apparatus 301, typically an X-ray apparatus, where undesired objects in the primary stream are detected. The detected undesired objects are then used as an operation parameter by a control unit to reject meat pieces by a first reject device 360 containing the undesired objects from the primary stream.

In the embodiment shown here, the first reject device 360 comprises a cutting device 302 similar as e.g. discussed in relation to FIGS. 1 and 2, for cutting a meat strip around the undesired objects, and a reject unit 306 for rejecting the meat strip onto an underlying recirculation apparatus driven by at least one motor unit 307 that receives and recirculates the rejected meat pieces as a secondary stream into the radiation inspection apparatus. As will be discussed in more details later, the radiation inspection apparatus is further configured to detect undesired objects in the secondary stream and automatically reject the detected undesired objects in the secondary stream via a second reject device. As shown here, a chute 309 or the like may be arranged below the reject to receive and guide the reject to a reject area 303. From the reject area, the reject may be conveyed by a conveyor device such as an auger 304 to a further processing area 305 where an operator 318 may manually remove the undesired objects therefrom and place the remaining meat pieces back into e.g. the secondary stream via e.g. an opening 404. This may then be repeated in case additional undesired objects are detected.

Figure 5:
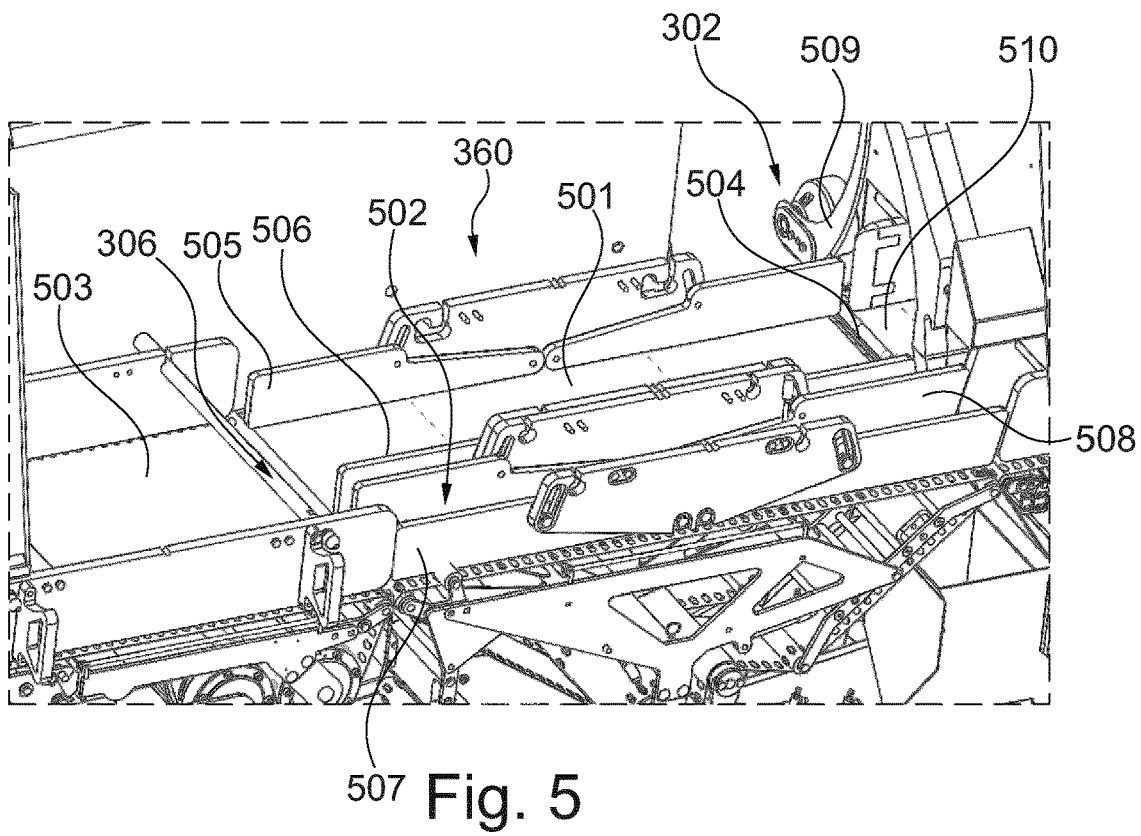
FIGS. 5 and 6 show two different perspective views of another embodiment of a system according to the present invention for processing meat pieces.

FIG. 5 shows a zoomed up view of the first reject device 360 showing a conveyor arrangement, also referred to as a first conveyor device, for conveying the primary stream of meat pieces, and the reject unit.

The conveyor arrangement comprises several end-to-end arranged conveyors, or as shown here, a conveyor 510 passing through the radiation inspection apparatus 301, a conveyor 501 where the space 504 between the ends of these two conveyors defines the cutting plane of the knife 509 of the cutting device 302, and a conveyor 503 arranged in an end-to-end arrangement with conveyor 501, where the end-to-end arrangement defines a reject unit 306. As shown here, walls 505, 506 are provided to ensure that the primary stream of meat pieces is preserved on the first conveyor device.

In another embodiment not shown here, a reject unit could also be arranged adjacent the end of conveyor 510 such that a temporal space is created between the end of the conveyor 510 such that impact from the cutting knife 509 causes the cut parts from the primary stream to immediately drop down and be rejected from the primary stream. By doing so, the overall size/length of the system may be reduced because the conveyor 501 may in that sense not be necessary and instead, conveyor 503 may be arranged adjacent to conveyor 510 and thus act as a take-away conveyor.

Shown is also a second conveyor device 502 for the secondary stream of meat pieces comprising two or more end-to-end arranged conveyors, where walls 507, 508 are provided to ensure that the secondary stream of meat pieces is preserved on the second conveyor device.

Figure 6:
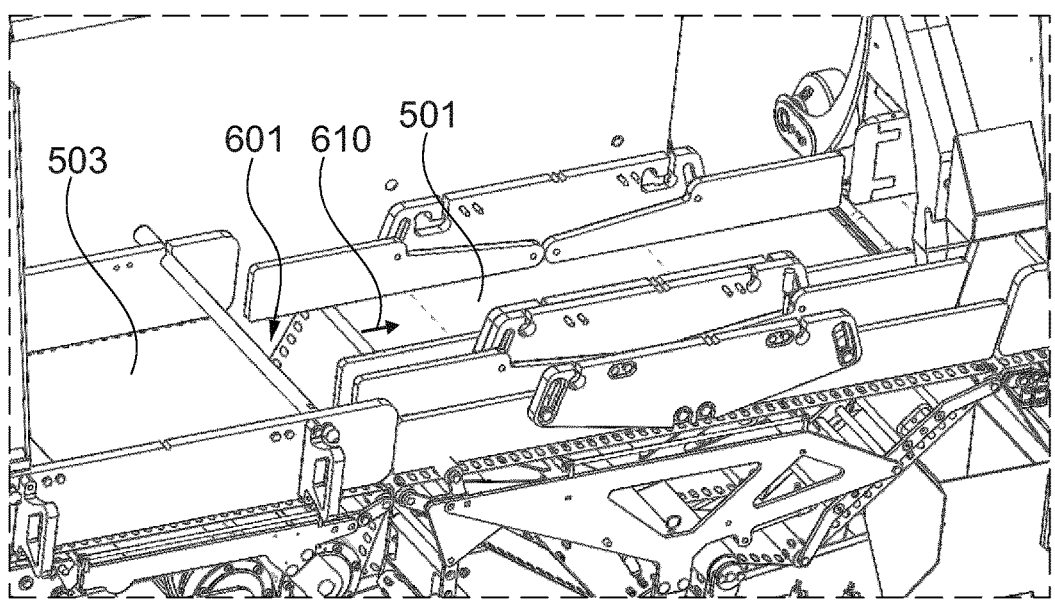

FIG. 6 shows where the reject unit 306 in FIG. 5 creates a temporal opening 601 by advancing, via an advancing mechanism connected to the end of conveyor 501 facing conveyor 503, the end of conveyor 501 backwards against the conveying direction of the primary stream as indicated by the arrow 610 to allow meat pieces, typically a strip of meat cut by the knife 509 containing the undesired objects, to be rejected from the primary stream onto the underlying recirculation apparatus.

Figure 7:
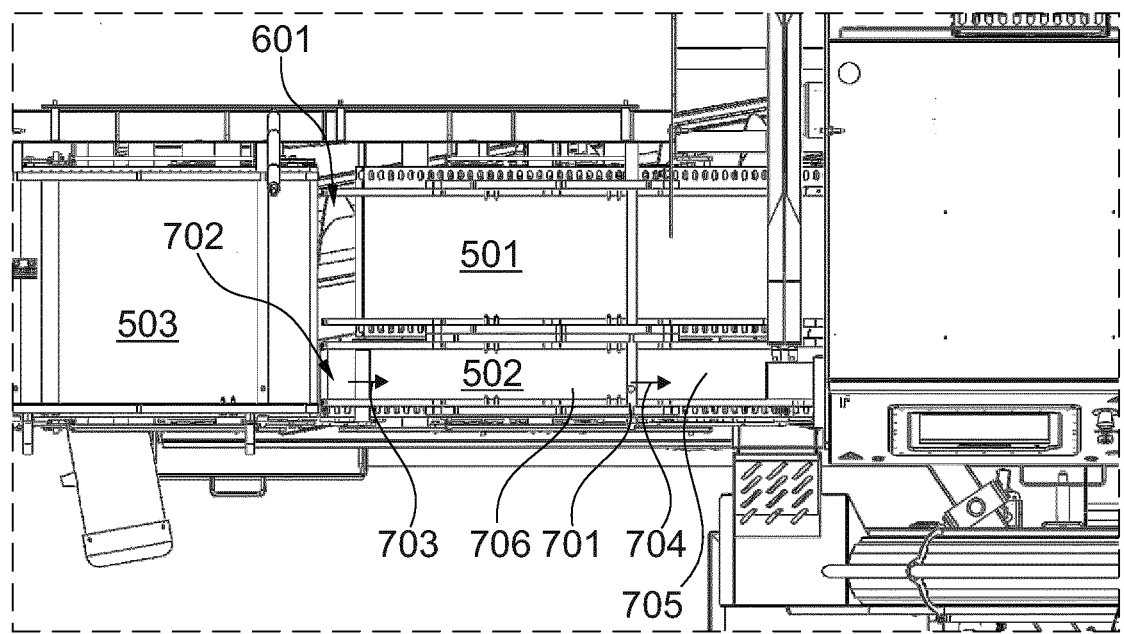
FIG. 7 shows a top view of FIGS. 5 and 6.

FIG. 7 shows a top view of FIGS. 5 and 6 showing in more details the side-by side arranged first and second conveyor devices 501, 502 showing the first conveyor device 501 in the open position as shown in FIG. 6.

The second conveyor device 502 comprises a conveyor 705 that conveys the secondary stream through the radiation inspection apparatus 301, conveyor 706 is arranged in an end-to-end arrangement with conveyor 705.

The second reject device 701 in the embodiment comprises a moving mechanism connected to the free end of e.g. conveyor 705 for moving the free end in a direction as indicated by arrow 704 when rejecting undesired objects, or meat pieces containing undesired objects, automatically from the secondary stream via the opening (not shown here), similar as discussed in relation to FIGS. 1 and 2. Said chute 309 receives the reject and guides it to said reject area 303 as discussed in relation to FIGS. 3 and 4. The reject, which typically is still some meat pieces containing undesired objects such as bones, are then recirculated as discussed in relation to FIG. 3.

In this embodiment, a further second reject device 702 is provided downstream in relation to the second reject device 701 but to sole purpose of this reject is to reject undesired objects such as metal or glass, that are not allowed to be recirculated into the system and instead to be removed immediately from the system. This second reject may work in a similar way, namely by moving the free end of the conveyor in a direction as indicated by arrow 703. Otherwise, the meat pieces in the secondary stream are received by conveyor 503 that acts as a common take-away conveyor for the first and second conveyor devices.

Figure 8:
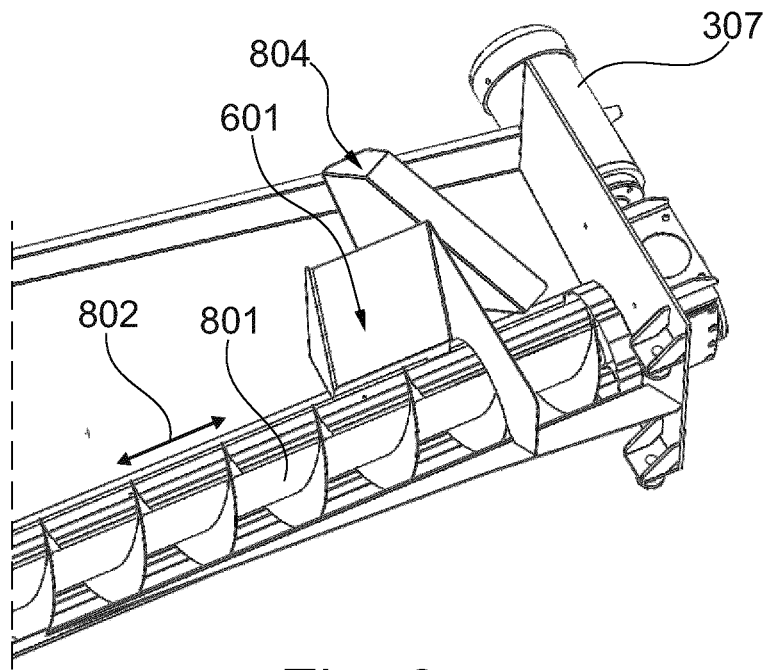
FIG. 8 shows a part of the recirculation apparatus according to the present invention.

FIG. 8 shows a part of the recirculation apparatus where the rejected meat pieces from the primary stream containing the undesired objects are guided to a first conveyor device, in this case an auger 801 that is driven by the motor 307 in a back and forth direction as indicated by arrow 802. The direction to the left in the view shown here is the recirculation direction, whereas the opposite direction is no recirculation but an immediate reject, e.g. because the rejected meat pieces contain glass, metal etc. as discussed in relation to FIG. 7 where undesired objects are rejected by the further second reject device 702 into a guiding member or a chute 804 that guides the reject out of the system. This immediate reject feature with the further second reject device 702 may however be considered as being an optional feature.

Figure 9:
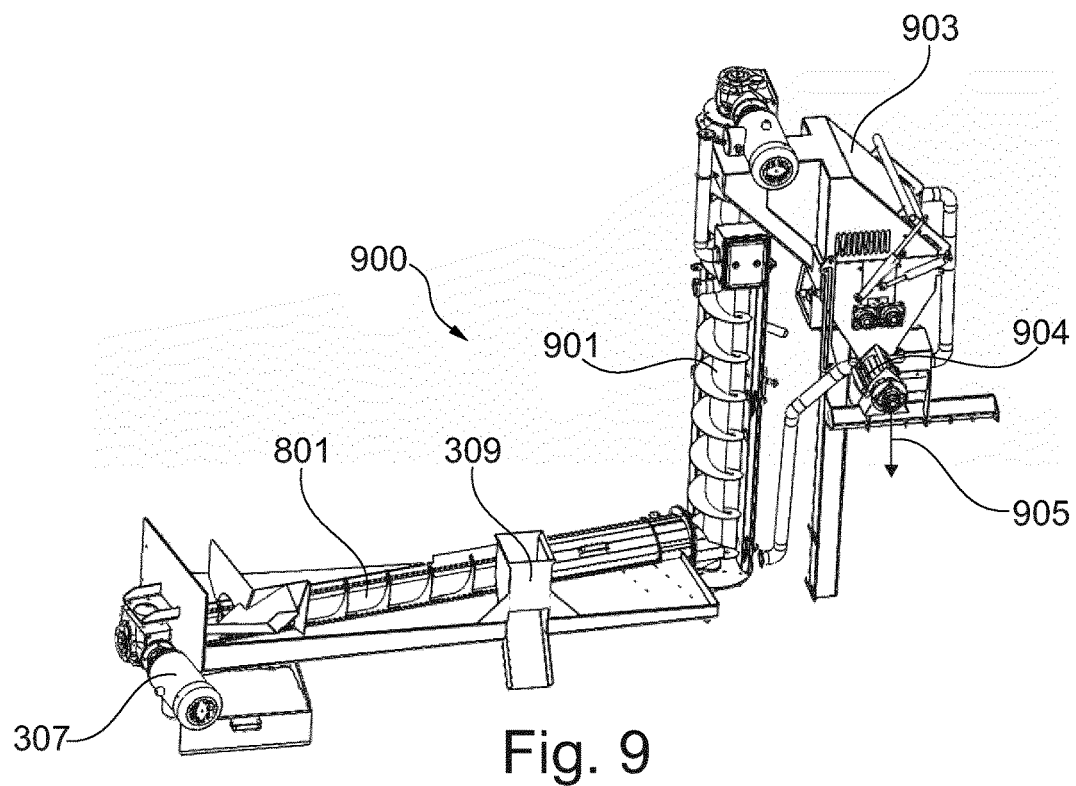
FIG. 9 shows a perspective and isolated view of the recirculation apparatus (in the absence of housings)

FIG. 9 shows a perspective and isolated view of the recirculation apparatus 909 discussed in relation to the embodiment of FIGS. 3 to 8 in the absence of the housings shown in FIGS. 3 and 4. As shown here, the recirculation apparatus 900 comprises the auger 801 from FIG. 8, that conveys the rejected meat pieces containing the undesired objects from the primary stream to a second auger 901 positioned vertical (or askew). The second auger 901 receives the rejected meat pieces and conveys them upwards to a receiving facility 903. At the receiving facility 903 the received rejected meat pieces may slide downwards to a distributing apparatus 904 that generates the secondary stream as a substantially even stream or a stream of separated rejected meat pieces. These are released as indicated by the vertical arrow 905 onto said second (secondary) conveyor device and defines said secondary stream. Shown is also said chute 309 shown in FIG. 3 arranged below the second reject device (not shown).

Figure 10:
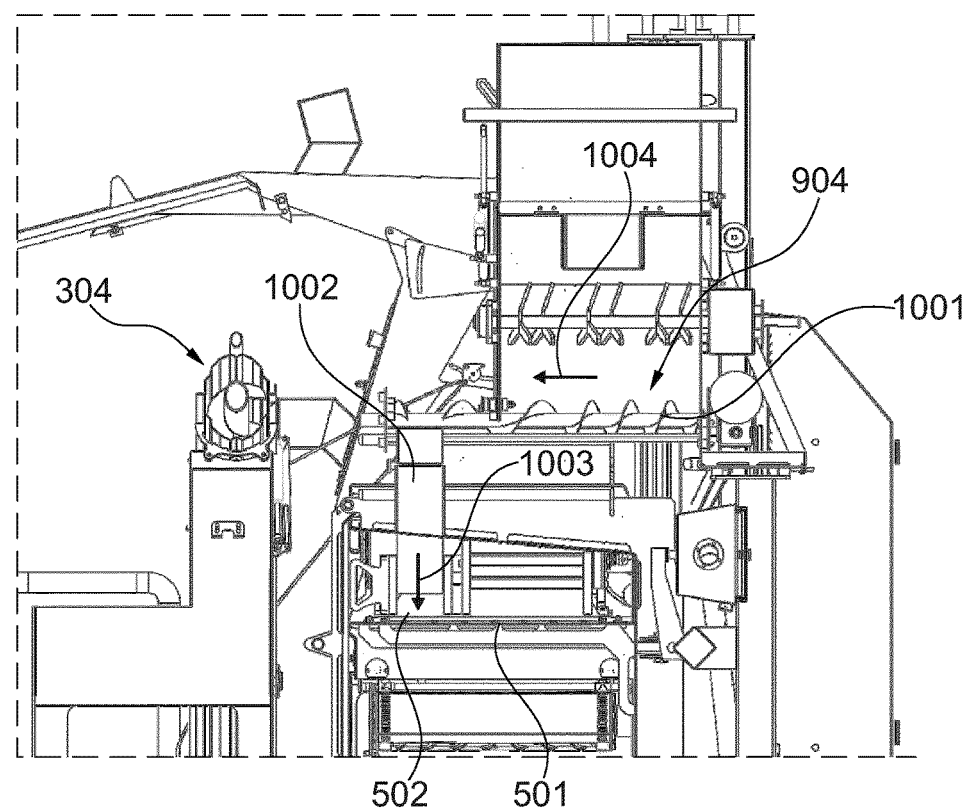
FIG. 10 shows a back/side view of FIG. 9.

FIG. 10 shows a back/side view of FIG. 9, showing the distributing apparatus 904 in more details in the absence of the housing, where the distributing apparatus 904 comprises a horizontally arranged auger 1001 that is preferably fully controllable and that receives the rejected meat pieces from the receiving facility 903 and conveys it in a horizontal direction as indicated by the horizontal arrow 1004 to a receiving area 1002, which may comprise a vertically arranged funnel or chute or the like arranged above said second conveyor device 502, that releases the rejected meat pieces on the second conveyor device as indicated by the vertical arrow 1003. Shown in this backside view is also said first conveyor device 501.

Figure 11:
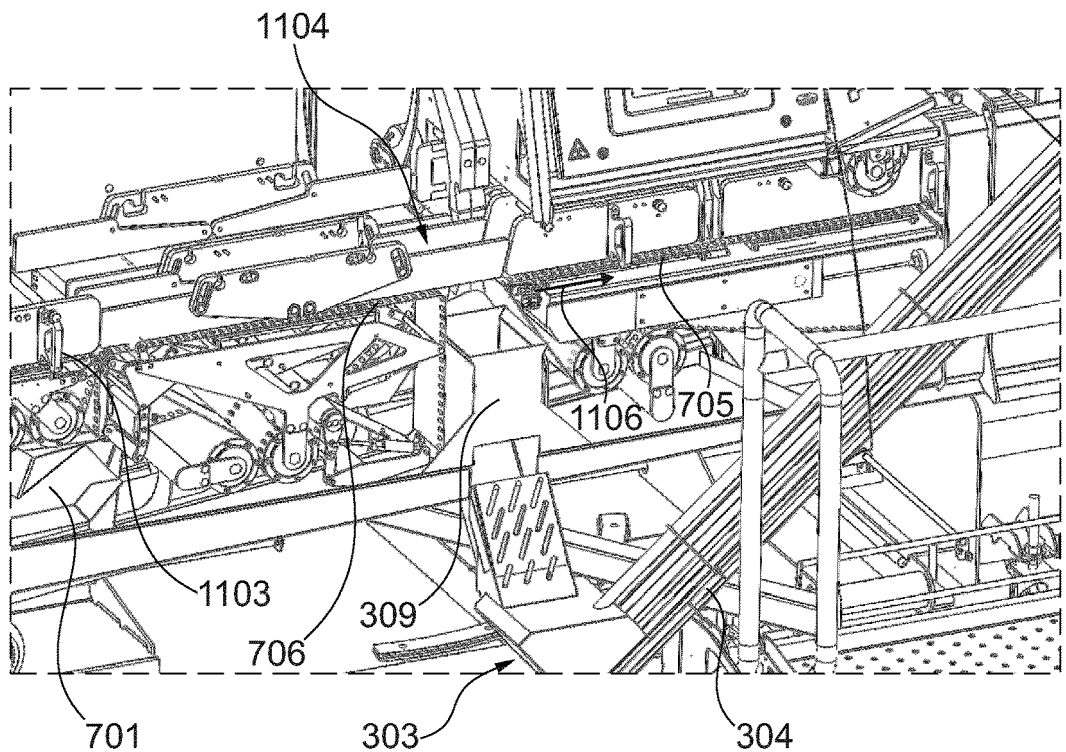
FIG. 11 shows a zoomed up view of a second reject device according to the present invention.

FIG. 11 shows a zoomed up view of the second reject device 701 second conveyor device 502 discussed in particular in relation to FIG. 7, where the rejected undesired objects from the secondary stream is released through the opening between said conveyors 705, 706 using the detection of the undesired objects in the secondary stream as an operation parameter. Shown is also said further second reject device 702 discussed in relation to FIG. 7.

Figure 12:
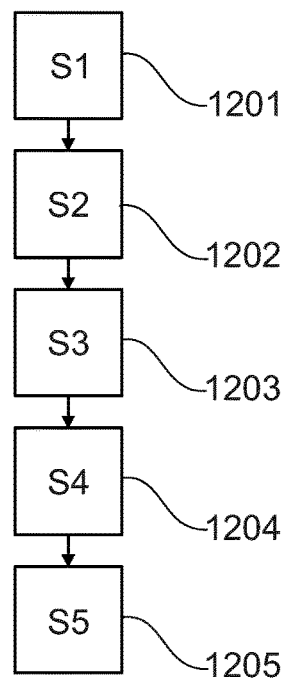
FIG. 12 shows a flowchart of a method according to the present invention.

FIG. 12 shows a flowchart of an embodiment of a method according to the present invention of processing meat pieces.

In step (S1) 1201 a primary stream of meat pieces are received, typically such that the primary stream essentially forms a continuous layer having an essentially even thickness.

In step (S2) 1202, the primary stream is conveyed though a radiation inspection apparatus, e.g. an X-ray, where meat pieces containing undesired objects are detected.

In step (S3) 1203, the detection of the undesired objects is used as an operation parameter in rejecting the meat pieces containing the undesired objects from the primary stream of trim products. In one embodiment, this may comprise cutting a piece from the primary stream, e.g. a slice that contains the undesired object(s). The separation may include dropping the cut part containing the undesired object(s) onto e.g. an underlying conveyor, or any kind of separation device may be used, e.g. a robotic system.

In step (S4) 1204, the rejected meat pieces are recirculated into the radiation inspection apparatus as a secondary stream meaning that two parallel streams, i.e. the primary and the secondary streams are conveyed through the radiation inspection apparatus. This recirculation may be performed as discussed in relation to FIGS. 1 to 11.

In step (S5) 1205, undesired objects are detected in the secondary stream and preferably automatically removed therefrom, e.g. via the second reject device discussed in relation to FIG. 1.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A system for processing meat pieces, comprising:
a radiation inspection apparatus configured to receive a primary stream of meat pieces and to detect undesired objects in the primary stream;
a first reject device;
a control unit configured to operate the first reject device using the detection of the undesired objects as an operation parameter such that meat pieces containing the undesired objects are rejected from the primary stream;
a recirculation apparatus comprising one or more conveyor devices configured to receive and recirculate the rejected meat pieces as a secondary stream of meat pieces into the radiation inspection apparatus, the radiation inspection apparatus further being configured to detect undesired objects in the secondary stream of meat pieces; and
a second reject device, operated by the control unit using the detection of the undesired objects in the secondary stream as an operation parameter, the second reject device being configured to reject the undesired objects from the secondary stream of meat pieces;
wherein the radiation inspection apparatus is configured to simultaneously detect undesired objects in both in the primary stream and secondary stream.

2. The system according to claim 1, wherein the first reject device cooperates with a cutting device positioned between the radiation inspection apparatus and the first reject device, where the cutting device is configured to cut parts from the primary stream, where the meat pieces containing the undesired objects are the cut parts.

3. The system according to claim 2, wherein the first reject device further comprises a spacer for creating a temporal spacing adjacent to a cutting plane of the cutting device so as to allow the cut parts to be rejected simultaneous to the cutting.

4. The system according to claim 1, further comprising an object remover configured to remove undesired objects from the rejected meat pieces prior to entering radiation inspection apparatus as the secondary stream.

5. The system according to claim 1, wherein the recirculation apparatus comprises a distributing apparatus configured to generate the secondary stream as a substantially even stream or a stream of separated rejected meat pieces.

6. The system according to claim 5, wherein the distributing apparatus comprises an auger device.

7. The system according to claim 1, wherein the radiation inspection apparatus comprises at least one X-ray apparatus.

8. The system according to claim 1, wherein the remaining meat pieces in the primary stream and the secondary stream are conveyed to a common receiving area by at least one conveyor.

9. The system according to claim 1, wherein the primary stream of meat pieces is conveyed by a first conveyor device and the secondary stream by a second conveyor device.

10. The system according to claim 1, wherein the one or more conveyors including at least one horizontal arranged conveyor, or at least one vertical arranged conveyor, or an askew arranged conveyor, or a combination thereof.

* * * * *

UNITED STATES PATENT AND TRADEMARK OFFICE
CERTIFICATE OF CORRECTION

| | | |
|---|---|---|
| PATENT NO. | : 11,533,920 B2 | |
| APPLICATION NO. | : 16/349491 | |
| DATED | : December 27, 2022 | |
| INVENTOR(S) | : Arni Sigurdsson and Agust Örn Einarsson | |

It is certified that error appears in the above-identified patent and that said Letters Patent is hereby corrected as shown below:

In the Claims

Column 12, Line 30:
Change "detect undesired objects in both in" to -- detect undesired objects both in --

Signed and Sealed this
Thirteenth Day of June, 2023

Katherine Kelly Vidal
*Director of the United States Patent and Trademark Office*